United States Patent [19]
Waigh et al.

[11] Patent Number: 5,380,514
[45] Date of Patent: Jan. 10, 1995

[54] METHOD FOR MAGNETIC RESONANCE IMAGING OF INTERNAL BODY TISSUES USING POLYSILOXANES

[75] Inventors: Roger D. Waigh, Wilmslow; John T. Fell, Lymm; Sylvia J. Anie, London; Brian Wood, Manchester, all of England

[73] Assignee: The Victoria University of Manchester, Manchester, England

[21] Appl. No.: 934,692

[22] PCT Filed: Mar. 21, 1991

[86] PCT No.: PCT/GB91/00431
§ 371 Date: Dec. 24, 1992
§ 102(e) Date: Dec. 24, 1992

[87] PCT Pub. No.: WO91/14457
PCT Pub. Date: Oct. 3, 1991

[30] Foreign Application Priority Data

Mar. 24, 1990 [GB] United Kingdom ............ 9006671

[51] Int. Cl.$^6$ .............. A61B 5/055; C08G 77/00; C08G 77/04
[52] U.S. Cl. ................... 424/9; 436/173; 128/653.4; 528/10; 528/29
[58] Field of Search ............ 424/9; 436/173; 128/653.4, 654; 528/10, 29

[56] References Cited
U.S. PATENT DOCUMENTS

| | | | |
|---|---|---|---|
| 4,136,250 | 1/1979 | Mueller et al. | 528/29 |
| 4,729,892 | 3/1988 | Beall | 424/9 |
| 5,143,716 | 9/1992 | Unger | 424/9 |
| 5,205,290 | 4/1993 | Unger | 128/653.4 |

FOREIGN PATENT DOCUMENTS 0133603 2/1985 European Pat. Off. .
0186616 7/1986 European Pat. Off. .
8800060 1/1988 WIPO .

OTHER PUBLICATIONS

STN File Server, Accession No. 317955, Bioses, vol. 87, M. Friedrich et al: "MR-Tomography of the breast additional information in selected cases", & Radiologe, vol. 27, No. 4, (1987), Coden: RDLGBC ISSN:, pp. 165–177.

Primary Examiner—Gary E. Hollinden
Attorney, Agent, or Firm—Cushman, Darby & Cushman

[57] ABSTRACT

Method for examination of internal body tissues by NMR (nuclear magnetic resonance) imaging procedures, and especially for examination of the alimentary tract, by administering an inert proton-rich organo-silicon polymer as a contrast medium within the body of the subject to be examined. The polymer is preferably a polysiloxane, especially a dimethylsiloxane. It can be administered easily as an emulsion, and is inert, non-toxic, and not absorbed or degraded in the living body. It overcomes the disadvantages of known imaging techniques using a contrast agent or opacifying agent which relies upon introduction of a metal derivative, which can have undesirable side-effects. It can be used without the need for image enhancement techniques (e.g. with older NMR equipment) as well as with more modern equipment. The method can give consistent and high quality imaging results and used as a part of a diagnostic method in the study of soft internal body tissues and cavities, as it gives selective contrast to the gut contents (for example the colon, duodenum and other parts of the alimentary tract).

6 Claims, No Drawings

METHOD FOR MAGNETIC RESONANCE IMAGING OF INTERNAL BODY TISSUES USING POLYSILOXANES

This invention relates to a method for study of internal body tissues (i.e. the tissues themselves and cavities within them), and more particularly to a method for the non-invasive examination of internal body tissues by nuclear magnetic resonance imaging procedures, and especially for examination of soft body tissues for example the alimentary tract.

Nuclear magnetic resonance is conventionally referred to, for convenience, as "NMR."

It is known to examine internal body tissues and cavities by a variety of techniques, among which the examination by X-ray techniques is most widely used. This depends upon the extent to which the body tissues and cavities can be differentiated from each other, and this can be difficult, especially for soft tissues. Even the use of opacifiers to produce "shadows" or image contrasts in the regions of interest are not sufficiently satisfactory for many clinical purposes. This problem is most marked in dealing with non-invasive examination of the gut (for example the bowel) but is evident for other body tissues too.

More recently, NMR has been proposed as a method for imaging certain parts of the body. It has been proposed to use imaging techniques in which a contrast agent or opacifying agent is used, which is chosen to be a compound which has the property of enhancing the NMR response signal when in the body. Unfortunately, the compounds so far proposed are not entirely satisfactory for the purpose. These are compounds derived from metals (e.g. iron, manganese, gadolinium) and, though they have the desired NMR characteristics, their properties with respect to the body of a patent can be undesirable, so that their use is not attractive. For example, such materials have the disadvantages that the metal-based compounds can produce undesirable side-effects on the patient to whom they are administered, for example diarrhoea and flatulence. Some patients therefore cannot tolerate these imaging media (contrast agents) to an acceptable degree.

We have found that this problem can be overcome by use of selected organo-silicon polymers as contrast agents or media.

Thus according to our invention we provide a method for the study of internal body tissues by nuclear magnetic resonance imaging techniques which comprises the step of administering an inert proton-rich organo-silicon polymer as the contrast medium within the body of the subject to be examined.

In such polymers, the silicon is chemically bound to organic groups, usually hydrocarbon groups. The polymers can be referred to by a variety of names, for example as "organic silicon-containing polymers," "silicon-containing organic polymers" or "silicones," but the term "organo-silicon polymers" is used herein to make it clear that the silicon is chemically bound and is not merely mixed in as a separate component (e.g. in elemental form).

The inert proton-rich organo-silicon polymer used for the purposes of the present invention may be especially one or more of those known as polysiloxanes. These are polymers having a series of units linked by silicon-oxygen bonds and with organic substituents on the silicon atoms. These organic substituents contain the hydrogen atoms which produce the NMR image.

Thus, especially, we provide according to our invention such a method in which the organo-silicon polymer used as the contrast medium is a polysiloxane.

The properties which make organo-silicon polymers, and especially a polysiloxane, useful for this purpose are:

(a) the compounds show strong single-line signals with a different chemical shift and relaxation time differences from those of body tissues. Both the chemical shift and relaxation times can be utilised to give selective contrast to the gut contents or other body tissues;

(b) the compounds lack taste and odour, and are completely inert chemically and physiologically towards body tissues, and have a low absorbability in the animal body. They also have a long history of previous use for medical proposes without any evidence of adverse properties or effects.

Accordingly, our invention also comprises the use as a contrast medium in the study of internal body tissues by nuclear magnetic resonance imaging, of an inert proton-rich organo-silicon polymer. Further, it also comprises the use of an inert proton-rich organo-silicon polymer in the preparation of a composition for use as a contrast medium for nuclear magnetic resonance imaging, in which the said polymer functions as the contrast agent.

The organo-silicon polymer or polysiloxane may be any such compound having a convenient structure or other properties which facilitate its use according to the present invention. Thus the structure of the polysiloxane (e.g. a polydimethylsiloxane) may be any which it is convenient or feasible to make, and may for example be linear, branched or cyclic, or any combination of such structures. Likewise, it may be a homopolymer or copolymer, and may be of any desired molecular weight and physical properties, for example viscosity. The invention is not necessarily restricted to the use of these, and any other forms of proton-rich organo-silicon polymers may be used if desired.

The choice of the organo-silicon polymer and the form in which it is used may be made by simple trial. This can be done very conveniently from among those products already available or obtainable commercially without the necessity to make any special product to achieve effectiveness.

It is usually most convenient and preferred to use compounds in which the substituents on the silicon atoms are methyl groups, as methyl groups (by the H-resonance of the $CH_3$ groups) give the strongest NMR signals, but other hydrocarbon substituents may be present if desired and are not necessarily to be excluded.

The polysiloxane used for the purposes of our invention is preferably a poly-dimethylsiloxane ("PDMS"), as they combine the properties of having a high proportion of substituents giving a strong NMR signal and are also most convenient and commonly available commercially. Such compounds are readily available in commerce and are already used for medicinal purposes, for example as components of dyspepsia remedies, in which they are taken internally; they are thus well-known and widely used and known to be biologically safe materials.

The structure of a polydimethylsiloxane is usually a chain of —Si(CH$_3$)$_2$- groups alternating with oxygen atoms and terminated by —Si (CH$_3$)$_3$ groups.

The organo-silicon polymers have the advantage that their higher molecular weight forms are not absorbed or degraded in the living body. Such polysiloxanes, for example, are proton-rich substances which have useful NMR imaging properties and are also inert (or substantially so) towards the body tissues and the patient.

The body tissues can then be examined by NMR techniques when the imaging medium is in place in the region to be examined.

The NMR techniques may be any of those known in the art, and in general do not need to be modified on account of our choice of new imaging material. Any adjustments which may be made to the method of using the NMR equipment are those which would be well within the skill and judgement of the expert in the art of NMR imaging.

Older equipment, for example, may be used in standard manner and in general without any need for image enhancement techniques. In such cases, the examination would benefit by the presence, as a result of the use of our invention, of a larger number of protons in the subject's body mass where otherwise there would be empty space. The conventional T$_1$ and T$_2$ weighting techniques may be used in studying and/or assessing the imaging results.

More modern and powerful equipment can benefit further from their ability to use the different resonance frequencies due to H$_2$O (water) molecules and to the hydrogen atoms in the organic polymer (especially the hydrogen atoms bound as part of alkyl groups—especially methyl groups), and to set up from these separate images for these two. This enables the study of the imaging results to allow further differentiation between the materials within a body, so that closer and more detailed examinations may become possible. The conventional T$_1$ and T$_2$ weighting techniques may be used, but are more likely to benefit from T$_2$ weighting as higher field strengths are used.

The field strengths for the NMR study may vary considerably, for example in the range 0,3 to 4.7 Tesla, and even outside this range if desired.

Strong resonance lines are observed during NMR, and these are shifted from those of protons associated with water to those associated with the organo-silicon polymer. These "chemical shift" differences can be utilised to give selective contrast, for example for bowel marking. Furthermore, the relaxation times of organo-silicon polymer samples, when significantly different from those associated with body tissues will enable contrast to be observed in images. Thus our invention may be operated by the chemical shift imaging technique or the relaxation measurement technique, or by combinations of these.

The magnitude of the "chemical shift" varies according to a variety of factors. One of these is the field strength (B$_o$) and at high field strengths can be very significant. For example, the protons of a sample of PDMS resonate at a different frequency from those protons of water, so that the NMR spectrum of a mixture of water and PDMS shows two peaks and there is a shift of approximately 867 Hz between them. The peak areas give an an indication of the relative amounts of the two chemical species.

In imaging, there can be a problem on account of the images of PDMS being displaced relative to the images of water. This is termed "the chemical shift artefact," and has to be allowed for.

A new method of eradicating this chemical shift artefact, based on that proposed by Vilk et al., 1987, can be used. This is referred to as the Chemical Shift - Specific Slice Selection, or C4S technique. The transmitter is set to the chemical species under consideration, e.g. water protons. A slice-selective 90° pulse is applied to the system in the presence of a slice selecting gradient, G$_z$, and two slices of the sample are excited; a slice of PDMS protons and a slice of water protons. Following this, a 180° pulse is applied during which G$_z$ is reversed, i.e. of the same amplitude but of opposite sign to that employed in the 90° pulse. No signal is produced from the PDMS slice because G$_z$ has been reversed, and therefore another slice not corresponding to the initial excited PDMS slice has been subjected to the 180° pulse. Thus, only the slice of water protons is subject to both the 90° and 180° pulses, producing a water-selective image. The method proved successful during, for example, imaging of the rat abdomen containing PDMS. The images so obtained did not suffer from the drawbacks of chemical shift artefacts. PDMS-selective images showed areas containing PDMS, for example the gastro-intestinal tract. These images also depicted areas of fat because the protons of fat resonate at a frequency close to the protons of PDMS.

The administration of the organo-silicon compound (e.g. a polysiloxane) may be achieved by using the polymer in any form which is sufficiently mobile to allow it to be introduced into the region to be studied and to remain there sufficiently long for the study to be carried out. Thus it may be administered as a liquid polymer as such (conveniently referred to as "the pure polymer") alone or with additives. Alternatively it may be administered as a composition which has the desired physical properties and contains the organo-silicon polymer; such compositions may be formulated and adjusted to have the desired physical properties even if the "pure" polymer itself does not have these. For example, a polymer which is too fluid or too viscous alone may be made into a composition which does have a convenient viscosity. It is of practical importance that the polymer, or composition containing it, should have a degree of fluidity which facilitate the location of it where it is required and also contains sufficient of the polymer to facilitate its detection in the NMR procedure.

The organo-silicon polymer can be of a molecular weight which may vary within wide limits, and can have a viscosity which may also vary within wide limits. Thus, for example, the viscosity of the organo-silicon polymer may be in the range 0.65 to 100,000 centistokes, but materials outside this range may also be used if desired. For use, it is convenient for the polymer and/or the composition containing it to have a viscosity in the range 20 to 1000 centistokes, but materials outside this range may be used if desired.

It is usually sufficient to use a single organo-silicon polymer, but mixtures thereof may be used if desired.

Most conveniently, the organo-silicon polymer is use in the form of a dispersion or suspension in a liquid medium. These may be for example an emulsion, and especially in an aqueous medium. The methods and components for making such emulsions, or other forms of dispersions, are those well known in the art. For live subjects, they should be pharmaceutically acceptable components.

The organo-silicon polymers or compositions (e.g. emulsions) can be administered to the subject or patient by a variety of methods, provided they are acceptable and do not cause any adverse effects to the subject. The criteria for live subjects are obviously more stringent than for dead subjects. For example, and most conveniently for examination of the alimentary tract or the gastro-intestinal tract, they may be administered by oral or rectal procedures, but alternatives may be used if desired, for example introduction through a tube or other device which is inserted so that the polymer can be injected into the body or the tract at the position in which it is required to be effective and observed.

Though administration is most useful in the alimentary tract, the invention is also applicable to study of other regions of the body. For example, it may be used by introduction into any orifices, cavities, tubes, and the like to which access can be gained without harm. Examples include the genito-urinary system, where it may be used to facilitate study of the fallopian tubes, bladder and the like, where other agents may be less suitable. Likewise, so long as the method and the presence of the polymer can be tolerated, it can be injected (as such or as a composition containing it) into other sites, for example articulations and joints.

Such emulsions or dispersions can be made to have the desired degree of fluidity or viscosity which the user requires to enable the material to move as quickly or slowly as desired in that part of the body to be studied. This facility to allow the viscosity to be controlled over a considerable range can be most useful and an advantage of the present invention. Usually, if it is desired for the imaging material to reside in the desired place in a body cavity, the more viscous compositions (e.g. emulsions) are usually to be preferred.

In formulating the compositions for administration, the preparation of a suspension or emulsion may be carried out by conventional means using conventional pharmaceutically acceptable additives (e.g. dispersing agents, thickening agents, flavouring agents, colouring agents, preservatives, anti-bacterial agents and the like, and mixtures thereof) if so desired to make them more stable, or less bland and possibly more acceptable to the patients to whom they are administered.

The criteria are strict, of course, for the study of live subjects, but may be less so for the study of dead subjects. An advantage of the present invention is its suitability for the safe study of live subjects, but this does not exclude it from being valuable also for dead subjects.

The method and compositions of the present invention may be used for the examination of human or animal subjects, and may be used to examine them for normality or abnormality of function of any organ or region within the body to which the polymer can be introduced without damaging tissues.

The invention and compositions they may be used especially for imaging of the gut, for example the colon, duodenum and the alimentary tract. Consistent and high quality imaging results have been obtained, for example, in studies of rats without any harmful results to the animals.

The invention is illustrated but not limited by the following Examples, in which the parts and percentages are by weight unless otherwise stated.

EXAMPLE 1

Use of PDMS alone ("pure" PDMS) on a live rat, and showing chemical shift imaging.

The investigations utilised Sprague-Dawley male rats (200 g). The rats were either sacrificed prior to imaging by halothane suffocation or anaesthetised (urethane; intraperitoneal; 5% saline; 0.6 ml/kg).

Oral administration of PDMS (polydimethylsiloxane), 3 ml., was performed with a syringe attached to a curved, blunt-tipped needle with a bulb soldered on the end. The needle was inserted directly into the oesophagus of the rat and the PDMS was infused slowly over 10 seconds. The rats were then sacrificed or anaesthetised for immobilisation during the imaging procedure. Each rat was placed in a restraint cage and positioned in the birdcage coil. The animals underwent scanning in the birdcage coil tuned to the proton frequency of 200 MHz. The $B_o$ field was shimmed over the region of interest, i.e. the rat.

Proton images were obtained at 4.7 T prior to and after the administration of the PDMS. Four contiguous slices of 4mm thickness were acquired each in the transverse and coronal planes. After the administration of PDMS, chemical selective images were obtained. The PDMS-selective images indicated predominantly the areas of PDMS in the gastrointestinal tract of the rat. The water-selective images displayed the areas where fairly mobile water protons were localised in vivo.

The 90° and 180° RF pulses were applied for 200 us and 400 us respectively. All images consisted of 128×128 pixels. The total sequence time, TR was 843 ms and the time to echo, TE was 40.4 ms. Image acquisition for each selection of water-selective images was 4 minutes. The PDMS-selective images took longer to acquire and image acquisition was 6 minutes. The more important parameters employed during the acquisition of the water-selective and the PDMS-selective images are given in Tables 1.A and 1.B below.

TABLE 1.A.

| (The more important parameters used during the acquisition of the water-selective images.) | |
|---|---|
| Observation frequency | SFO = 200.376 Hz |
| Sweep width | SW = 12500 Hz |
| Acquisition time | AQ = 0.010 s |
| Number of signal averages | NE = 1 |
| Number of scans | NS = 512 |
| Data memory size | SI = 256 W |
| Receiver gain | RG = 8 |

TABLE 1.B.

| (The more improtant parameters used during the aquisition of the PDMS-selective images.) | |
|---|---|
| Observation frequency | SFO = 200.3756 Hz |
| Sweep width | SW = 12500 Hz |
| Aquisition time | AQ = 0.019 s |
| Number of signal averages | NE = 2 |
| Number of scans | NS = 512 |
| Data memory size | SI = 256 W |
| Receiver gain | RG = 16 |

The transverse and coronal images displayed were selected sections from multiple slices which were acquired. Two sections of the same slice were compared:
(i) a water-selective section acquired after the administration of PDMS.
(ii) a PDMS-selective section acquired after the administration of PDMS.

The water-selective images were obtained by setting the resonant frequency to that of the protons of water. Generally, the water-selective images delineate all water-containing structures within the slice being considered. The PDMS-selective images were acquired by setting the resonant frequency to that of the protons of the polydimethylsiloxane. The PDMS-selective images indicate the localisation of PDMS in areas of the gastrointestinal tract. The sections may be compared with the water-selective sections of the same slice. Generally, with the water-selective images, the presence of PDMS will not be detected and dark areas are visualised. The dark areas where PDMS is located appear bright in the PDMS-selective images. The effectiveness of the chemical shift selectivity is demonstrated by the almost complete separation of PDMS and water in the acquired images.

Study of the water-selective images obtained showed that several anatomical features are observable, for example abdominal wall, kidney and spinal canal, but delineation of the gastro-intestinal tract is difficult. There are signals of intermediate intensity originating from the intestinal area (lower right hand side) of the image. In contrast, the PDMS-selective image clearly depicts the intestinal regions. These appear as roughly circular and bright areas. The shape of the areas, i.e. circular, is typical of a transverse section through the intestinal loops. There is also a region of weak intensity observed on the image which probably originates from PDMS present in the stomach of the rat.

EXAMPLE 2

Use of PDMS emulsion on a live rat, and showing chemical shift imaging.

An emulsion of PDMS was prepared in the following manner:

Sorbitan tri-oleate (Span 85), 0.38 ml, was measured out into a vial and mixed with the PDMS, 10 ml, in which 55 mg of propyl paraben had been dissolved. Methyl paraben (50 mg) was dissolved in polyoxyethylene 20 Sorbitan mono-oleate (Tween 80), 0.62 ml, and added to distilled water (3 ml) in a second vial. Both vials were then warmed to 40 degrees C. and stirred. The mixture of Tween 80 and distilled water was then added to the mixture of Span 85 and PDMS, and mixed for 40 minutes with a high speed shear mixer. The procedure was repeated with samples of PDMS of viscosity ranging from 20 to 1000 centistokes. The resulting emulsions were white and slightly viscous, and contained 71.4% of PDMS.

The relative amounts of the emulsifying agents (Span 85 and Tween 80) used were calculated from HLB (Hydrophilic-Lipophilic Balance) values. Of the samples investigated, a stable emulsion was obtained with a viscosity of 350 centistokes, and this was used during subsequent study.

The preparation of the animals was carried out as described in Example 1, with the exception that the emulsion and not pure PDMS was orally administered to the rats. The dosage of emulsion was 0.5 ml of the emulsion for a 200 g rat. This corresponds, for comparable contrast, to a dosage of 175 ml for a human weighing 70 kg.

The process of imaging was also as described in Example 1, and proton images were obtained at 4.7 T prior to and after oral dosing of the rats with the PDMS emulsion.

The 90° and 180° RF pulses were applied for 200 μs and 400 μs respectively. All images consisted of 128×128 pixels. The total sequence time, TR was 843 ms and the time to echo, TE was 40.4 ms.

The transverse and coronal images obtained/displayed were selected sections from multiple slices which were acquired. Two sections of the same slice were compared:

(i) a water-selective section acquired after the administration
of PDMS emulsion.
(ii) a PDMS-selective section acquired after the administration
of PDMS emulsion.

Generally, the water-selective images delineated all water-containing structures within the slice being considered. The PDMS-selective images discriminated the areas of the gastrointestinal tract in which the emulsion is present from those where the emulsion is absent. Because the emulsion contains water, weak signals originating from the presence of the emulsion were observed in the water-selective images.

EXAMPLE 3

Use of PDMS alone on a live rat, showing emptying of the stomach with time, and showing chemical shift imaging.

The proton image of the stomach in particular often appears as an indistinct black region. Furthermore, coronal, sagittal or transverse imaging may not always depict bowel loops and limited tissue contrast resolution may preclude the differentiation of the stomach and intestinal tract from contiguous structures. By use of polysiloxanes for contrast enhancement during nuclear magnetic resonance imaging, this problem can be overcome, and they are well tolerated without adverse physiological responses.

These studies used Sprague-Dawley rats (200 g) in an 18 hour starved state and anaesthetised with urethane (intraperitoneal; 5% in saline; 0.6 mg/kg).

Pure PDMS (2 ml) was administered orally to the rats which were then anaesthetised and each rat was placed in a restraint cage and positioned in the birdcage coil.

The animals underwent scanning at 200 MHz. Transverse sections of a selected slice were acquired at intervals after dosing of 10 minutes, 40 minutes, 700 minutes and 110 minutes after administration of the PDMS.

Observations of the scan images showed the stomach being filled with PDMS and then gradually with time the intensity decreases. In these images, the pylorus of the stomach was identified as is PDMS emptying into the duodenum. Similar images, but of a different slice, depicted the stomach, small intestine and duodenum. Ten minutes after administration of the PDMS, and intense signal was observed from the stomach and intestine. Seventy minutes after dosing the amount of PDMS in the stomach had greatly decreased and this feature was further enhanced 110 minutes after dosing.

Proton ($^1$H) NMR imaging can therefore be employed to observe the emptying of the stomach of PDMS and the distribution of PDMS in the bowel.

EXAMPLE 4

Illustrating Multislice Multiecho Sequence Imaging.

Using a Bruker Biospec 47/40 (4.7 T, 40 cm diameter bone), a series of phantoms were prepared containing animal fat, agarose, gel (to mimic muscle tissue), and samples of the silicone polymer of different viscosities.

Since Spin Echo images are insensitive to field inhomogeneities a series of $T_1$ and $T_2$ weighted images were obtained using the MSME (multi slices multi echoes) pulse sequence.

The results obtained show that by altering the TR and TE parameters a discrimination is observed between the silicone polymers and the other phantoms including between fat and the silicone polymers. Both forms of the silicone polymer show similar differentiation.

Using a Phillips Gyroscan SIS I.S.T. whole body imager and the MSME sequence as above, following oral administration of 3 ml of a pure siloxane polymer, images were obtained in which the presence of the polymer in the stomach of the animal is clearly observed compared to an image of taken in the same rat using the same pulse sequence before the administration of the polymer.

We claim:

1. In a method for the study of internal body tissues by nuclear magnetic resonance imaging which comprises administering a contrast agent to a subject to be examined and then applying nuclear magnetic resonance imaging to said subject, the improvement wherein the contrast agent consists of an inert proton-rich polysiloxane.

2. Method as claimed in claim 1 wherein the silicon atoms in the polysiloxane carry methyl groups as substituents.

3. Method as claimed in claim 1 wherein the polysiloxane is a polydimethylsiloxane.

4. Method as claimed in claims 1 wherein the polysiloxane is administered in the form of an emulsion or other dispersed form.

5. Method as claimed in claim 1 wherein the field strengths for the nuclear magnetic resonance study is in the range 0.3 to 4.7 Tesla.

6. Method as claimed in claim 1 which is used for imaging of the alimentary tract.

* * * * *